United States Patent [19]

Wolf

[11] 4,067,840
[45] Jan. 10, 1978

[54] SIGNAL COATING SUITABLE FOR LEAD-BASED PAINT HAZARD ABATEMENT OR THE LIKE AND FORMULATIONS THEREFOR

[75] Inventor: Richard E. Wolf, Prospect Heights, Ill.

[73] Assignee: DeSoto, Inc., Des Plaines, Ill.

[21] Appl. No.: 689,187

[22] Filed: May 24, 1976

[51] Int. Cl.$^2$ .......................... C08K 5/10; C08L 1/26; C08L 31/04
[52] U.S. Cl. .............................. 260/29.6 R; 252/365; 260/29.6 MN; 260/29.6 MQ; 260/29.6 MM; 260/42.21
[58] Field of Search ........................... 424/7; 252/365; 260/42.21, 29.6 R, 29.6 MM, 29.6 MQ, 29.6 MN

[56] References Cited

U.S. PATENT DOCUMENTS

| 3,935,137 | 1/1976 | Minkoff | 260/29.6 ME |
| 4,005,038 | 1/1977 | Minkoff | 260/29.6 ME |

FOREIGN PATENT DOCUMENTS 371,196  4/1932  United Kingdom.

Primary Examiner—Eugene C. Rzucidlo

Attorney, Agent, or Firm—Dressler, Goldsmith, Clement, Gordon & Shore, Ltd.

[57] ABSTRACT

Protective coatings, such as paints and liquid formulations therefor, containing a masked chromogen which signals contact with a body fluid when the protective coating is masticated or ingested are disclosed. The chromogen is capable of producing a contrasting color when masticated and/or ingested, thereby signaling that the individual who masticated and/or ingested the chromogen may have ingested an undesirable or hazardous substance, e.g., a lead-based paint, that has been covered by the protective coating. The chromogen is substantially indiscernible in the paint and converts by reaction with an activator substance, e.g., by reaction with saliva, gastric juices, or the like, to a colored form which then stains the body fluids and/or the body tissues, and which may also stain the original source of the undesirable substance. The chromogen may be a leuco base or a color base of a dye, or it may be a color indicator substance or a reagent specific to the undesirable or hazardous substance or to a body fluid component. Preferably the chromogen is present in the form of pressure-rupturable microcapsules that release the chromogen when masticated. If desired, an acerbic agent can be also incorporated into the protective coatings of this invention.

24 Claims, No Drawings

SIGNAL COATING SUITABLE FOR LEAD-BASED PAINT HAZARD ABATEMENT OR THE LIKE AND FORMULATIONS THEREFOR

BACKGROUND OF THE INVENTION

This invention relates to protective coatings containing a chromogenic signal means, for general application to all surfaces, but with special significance when applied over lead-based paint surfaces and the like hazards.

The ingestion of lead-based paint has been widely recognized as a major pediatric disease, especially among young children ranging in age from about one to about five years. Childhood lead poisoning is a problem that faces the health departments and housing officials throughout the Nation. The ingestion of paint chips, crumbling plaster, cracking wallpaper, and the nibbling of windowsills, frames and banisters by young children have been recognized as the principal causes of lead poisoning. The National Bureau of Standards has estimated that more than 600,000 children in the United States have dangerous levels of lead in their blood.

This problem is particularly acute in large metropolitan areas having homes constructed prior to 1940. White lead was the commonly utilized white pigment in that era and was present in both the interior and the exterior paints that were used at that time. Moreover, inasmuch as lead-based paints were commercially available as recently as 1972, a portion of homes built or redecorated up to that time are likely to contain some lead-based paint.

While the actions of governmental agencies and the paint industry have now limited the commercial availability of paints containing significant quantities of lead, the problem of homes and other structures coated with lead-based paint still exists.

Lead poisoning can result in several well-known but non-specific clinical syndromes of illness in man, some of which include anemia, loss of appetite, insomnia, muscle and joint pains, severe abdominal pain (lead colic) and headaches. However, in children such symptoms of lead poisoning are often overlooked or are erroneously attributed to other diseases. As a result, the poisoning due to lead is not likely to be recognized until a late or rather severe stage. Severe cases of lead poisoning or recurrent uncontrolled exposure to lead is responsible for progressive renal insufficiency and cerebral incompetency. Central nervous system effects have also been observed and in some cases, death.

The diagnostic tests for detecting lead poisoning are the measurement of blood lead concentration, spontaneous urinary lead excretion, and the Edathamil calcium disodium (CaEDTA) Mobilization Test, but by the time these are used on a child or are able to pick up the excessive lead concentration, some damaging injury may have already occurred.

In spite of the efforts made by municipal organizations to detect and treat the lead poisoning problem in young children it is believed that high percentages of cases go undetected. Control of the ingestion of lead-based paint is not only a desirable program but also is a necessary effort for minimizing the exposure of children to this hazard. To this end the National Paint and Coatings Association has prepared a considerable amount of material with a view toward educating the public in the prevention of lead poisoning. Their principal message has been to sweep up old, flaking paint chips or plaster from the wall and off the floor, and to provide the child with something safe to chew on. If the child is seen eating paint chips, the supervising adult is advised to take the child to the doctor, clinic or public health department immediately for appropriate treatment. While this is important advice, it is not sufficient for cases where children are unsupervised or not adequately minded.

Of course, the most effective method of preventing the ingestion of lead-based paints by a child would be to remove the paint from the wall. However, because of the age of the structures, the multiple number of paint coatings placed on top of the lead-based paint, as well as the difficulty and cost involved in lead-based paint removal, this method is generally considered inadequate. Also, removal of the coating by heating, sanding and scraping techniques imposes hazards of exposure to the workers involved in the paint removal program.

Other methods to abate the hazard of lead-based paint fall into the general category of covering up the hazardous surface with another, relatively permanent, barrier material. Wall structures can be covered with gypsum board or plywood, or other rigid covering materials. Windowsills, frames, banisters and railings can be covered with more flexible materials such as fabric, canvas or flexible membranes; however, such methods in many cases are costly and impractical.

The inclusion of a bad tasting substance, i.e., an acerbic agent, in a paint has also be reported in literature as a feasible approach toward solving the lead-based paint ingestion problem. It has been postulated that the bad taste of the covering paint will discourage the child from eating paint chips; however, evidence available to date has not shown that this particular approach provides an effective solution to the problem. Apparently, bad taste alone will not adequately discourage a small child.

It has also been proposed to cover lead-based paint with coatings containing emetics. While emetics may be effective, such a proposal appears to be of limited acceptability because of physical and/or psychological reasons. Moreover, the child may tolerate a small dose of emetic on a daily basis, or its effect may be ignored.

The use of chelating agents for the control of lead poisoning also has been reported. Edathamil calcium disodium (CaEDTA), 2,3-dimercapto-1-propanol (BAL) and d-penicillamine have been evaluated as therapeutic agents for this purpose. However, the oral administration of CaEDTA to acutely ill patients has been reported to be ineffectual and potentially harmful. Thus, the inclusion of chelating agents into a coating which would be used as a covering for lead-based paints has to be approached with considerable caution.

All of the heretofore proposed methods thus appear to have some major deficiency.

On the other hand, the present invention provides a completely different approach, namely, a signal indicating the ingestion of an undesirable substance which the parent or supervising adult cannot overlook. Thus, for example, the presently contemplated protective coatings can provide an early indication or signal that an individual may have ingested lead-based paint or a similar undesirable substance. As a result of this signal, appropriate prophylactic measures can be taken before the onset of poisoning symptoms. In addition, the present invention contemplates a hazard abatement method utilizing paint which would be applied during the normal course of renovation or redecoration utilizing conventional applicators and techniques. This is an inexpensive and practical procedure which can be followed by any family living in an older house which is suspected of having been painted with a lead-based paint.

SUMMARY OF THE INVENTION

The present invention contemplates the incorporation of an effective amount of a masked, physiologically acceptable chromogen into a coating formulation such as a conventional paint formulation, or the like, to provide a "signal coating" which serves as an early warning or detection system signaling the mastication and/or possible ingestion of an undesirable or toxic substance such as lead-based paint, or the like. The chromogen is capable of producing a distinctive, contrasting color when reacted with an activator substance such as saliva, gastric juices, or with the undesirable substance itself, thereby alerting a supervising adult that appropriate measures must be undertaken. Even if the adult does not know the source of the coloration, its presence on the child will attract attention and may provoke a medical examination.

The chromogen present in the coating formulation, and in the ultimately produced protective coating as a film of the formulation is deposited on a selected surface and dried, can be masked by the pigment that is present in the paint or by its being present in the paint in a colorless form. Alternatively and preferably, the chromogen can be incorporated into a paint formulation in a physically isolated form, e.g., in the form of rupturable or otherwise disintegratable microcapsules of appropriate opacity and masking pigmentation and which will release the chromogen upon mastication or which will disintegrate upon coming in contact with gastro-intestinal secretions. Mixed microcapsules containing chromogens responsive to different body fluids can also be used, as well as mixtures of microcapsules some of which contain the chromogen and others of which contain an activator substance for the chromogen.

In any event, in the preferred embodiment of this invention saliva and/or the gastro-intestinal juices serve as the activator substance in the presence of which the chromogen causes distinctive and contrasting color to appear around or in the child's mouth, in excreted body fluids and/or feces. Preferably, also the original source of the undesirable substance is stained so as to permit easy location thereof and to facilitate subsequent hazard abatement steps.

By the term "chromogen," as used herein and in the appended claims, is meant a substance which exists in a substantially colorless or in an indistinct or visually non-discernible form in the paint formulation or protective coating formed thereby, and which converts to a colored form upon reaction with an activator substance and stains a body fluid and/or tissue when ingested, and possibly also the source of the undesirable substance that has been masticated or ingested. Preferably the chromogen is a liquid or a water-soluble substance.

Suitable illustrative chromogens for the purposes of the present invention are white or colorless physiologically acceptable reagents that give color reactions when the components present in saliva or other body fluids, chelatometric indicators that are sensitive to the undesirable substance or to inorganic body fluid constituents, dye precursors such as leuco base or color base forms of dyes that give color reactions upon changed environmental conditions, other color indicator substances, and the like, which are soluble in such body fluids in sufficient concentration to give an identifiable coloration.

DESCRIPTION OF PREFERRED EMBODIMENTS

For the purposes of the present invention the composition of the paint formulation serving as a vehicle for the chromogen is not overly critical as long as the formulation and the ultimate protective covering derived therefrom adequately mask, i.e., render invisible or inconspicuous, the chromogen in the form that is present. Both interior paints and exterior paints can be used as signal carriers, though interior paints, and especially aqueous latex paints, are of special importance. Of course, the coating formulation must not trigger premature conversion of the chromogen to its soluble, colored dye or indicator form. To this end it is preferable to encapsulate the chromogen in a plurality of disintegratable microcapsules, preferably dissolvable or pressure-rupturable microcapsules, so that the chromogen remains dormant until the paint is masticated and/or ingested, i.e., until the signaling function is required. The microcapsules preferably can be disintegrated upon mastication even by infants without teeth, or dissolved in the infant's stomach or intestinal tract. Pressure-rupturable microcapsules that are not pH sensitive are preferred where the paint formulations may preactivate the chromogen to its colored form or where the formulations may tend to dissolve the encapsulated material.

Various methods of microencapsulation that are suitable for the present purposes can be categorized into three groups: phase separation or coacervation techniques, interfacial reactions, and physical methods. Each of these techniques follows substantially similar sequence of operations in forming the encapsulated product, namely (1) dispersion or emulsion formation, (2) capsule wall deposition, and (3) capsule isolation.

Coacervation or phase separation techniques usually comprise first forming a liquid wall about a discontinuous phase in a two-phase emulsion system by adjusting an independent variable such as temperature, composition, pH, or the like, and subsequently hardening the liquid wall. The encapsulated material, in this particular case the chromogen or chromogen-plus-appropriate carrier or vehicle therefor, is present in the discontinuous phase. Preferably the diameter of the chromogen-bearing microcapsules does not exceed about 25 microns, more preferably about 3 to about 10 microns, in order to facilitate dispersion in the coating formulation. The encapsulating material is selected to be compatible with the particular paint or protective coating, to be physiologically compatible and also to permit sufficient washability, and to provide abrasion resistance, impact resistance, and the like, of the applied coating without a premature activation of the chromogen. Suitable encapsulating materials are pharmacologically acceptable natural macromolecular substances such as gelatin, acacia, tragacanth, and the like, as well as synthetic macromolecular moieties such as polyethylene imine homopolymers or copolymers of amine-functional monomers, e.g., dimethylaminoethylacrylate, dimethylaminomethylacrylate, and the like.

The foregoing encapsulating materials can be further protected from the paint formulation or ultimate end use environment by providing an additional outer covering or shell thereover. It is particularly preferred to use amine copolymers insoluble in the aqueous alkaline medium of a typical latex paint, but soluble in stomach acids. Likewise, the materials presently utilized for microencapsulation of time-release medication are eminently suitable for microencapsulation of chromogens in accordance with the present invention.

The chromogen, if in liquid form, can be microencapsulated directly, or if in solid form, can be first dissolved or suspended in an inert liquid vehicle. Depending on the chromogen involved, the vehicle can be oil, water, alcohol, or other organic solvent. The liquid vehicle is selected so as not to trigger the conversion of the chromogen to its colored form during microencapsulation. The liquid vehicle containing the chromogen is then separated into a plurality of droplets which are provided with a rupturable wall or sheath. Suitable coacervation processes are taught in U.S. Pat. No. Re. 24,899 to Green, U.S. Pat. No. 3,137,631 to Soloway, U.S. Pat. No. 3,201,353 to Corbin, and U.S. Pat. No. 3,516,941 to Matson.

Another method of forming microcapsules is by interfacial polymerization. In this process, a monomer which is polymerizable to a solid is dissolved in a material in which the polymerized monomer is insoluble. This solution is then dispersed in a liquid in which neither the polymer nor the chromogen-bearing liquid is soluble. The presence of a catalyst and/or co-reactants in the continuous phase initiate polymerization in the interfacial regions around the chromogen-bearing liquid which is dispersed as the discontinuous phase. The polymer formed precipitates around the discontinuous phase, forming the desired microcapsule. This process can be employed using materials that polymerize by free radical mechanisms (e.g., styrene) and materials that polymerize by polycondensation. For example, the encapsulation of crystal violet lactone can be accomplished using styrene and divinyl benzene as the wall forming monomers with gum arabic as the emulsifier of the oil-in-water emulsion. Microencapsulation by interfacial polymerization is illustrated in U.S. Pat. No. 3,886,084 to Vassiliades and U.S. Pat. No. 3,429,837 to Ruus.

Solid chromogen particles can also be provided by coating solids particulate chromogenic materials directly with a protective sheath or coating that disintegrates upon ingestion. For this purpose the Wurster fluidized bed process, disclosed in U.S. Pat. No. 2,648,609 and U.S. Pat. No. 2,799,241 is suitable. Other suitable coating or encapsulation processes are disclosed in U.S. Pat. No. 3,891,572 to Moody et al. and U.S. Pat. No. 3,891,570 to Fukushima et al. Combinations of the aforedescribed microencapsulation techniques can also be utilized to provide more than one chromogen in the same microcapsule or to incorporate a chromogen and an activator substance therefor in separate portions of the same microcapsule, e.g., by providing a microcapsule within a microcapsule.

Particulate solids such as acicular titanium dioxide can also be employed as the carrier for the chromogen. If the chromogen is sensitive to the paint formulation in which the chromogen is to be introduced, the titanium dioxide particles carrying adsorbed or absorbed chromogen can be further provided with a protective sheath which is disintegratable upon ingestion. Other solid chromogen carriers suitable for the present purposes are silica, calcium carbonate, crystalline molecular sieves, and other adsorbent materials capable of providing a latent chromogen-carrier combination from which the chromogen is released when the combination is masticated and/or ingested. For latex-type paint formulations alkaline solid carrier materials, such as calcium carbonate, are particularly desirable.

In one embodiment of the present invention a chromogenic signal substance is incorporated into a water-based, latex-type interior paint which is substantially a stable dispersion in water of aqueous emulsion copolymers pigmented as desired to provide the coloration, and as needed to mask the chromogen that is present and to provide an opaque coating. The term "aqueous emulsion copolymer" as used herein and in the appended claims, denotes copolymers or interpolymers produced by the copolymerization of a liquid mixture of polymerizable monomers in an aqueous medium. For a stable dispersion, the polymerized product is colloidal, and preferably has a particle size of about 3 microns or less.

In another embodiment of this invention microcapsules containing different chromogens are admixed to provide a masked mixed chromogen combination which is incorporated into the paint and is responsive to different body fluids or ingestion conditions. For example, microcapsules containing an amino acid-sensitive reagent, such as ninhydrin, which reacts with the amino acids present in saliva can be admixed with microcapsules containing a leuco dye which is reactive with the gastric juices. Alternatively, microcapsules which contain substances which react with one another to form a distinctive color upon mastication can be used as well as microcapsules which contain a reagent which gives a color reaction with the undesirable substance, e.g., lead or lead oxide, when the reagent is released from the microcapsules in the presence thereof.

The preferred aqueous latex contains a small amount of an alkaline agent, usually ammonia, to provide an alkaline pH of from 7.5–10.5. These latex paints are normally sold white for pigmenting or otherwise coloring, as needed, so they are pigmented with titanium dioxide. Even when colorants are present, however, titanium dioxide usually constitutes the major weight proportion of the pigment. An embodiment of the present invention contemplates an aqueous latex coating composition that is alkaline and contains a chromogen in microcapsules that are insoluble in an alkaline medium but are soluble in an acidic medium such as gastric juice or the like.

The polymerizable monomers of choice for the latex are butyl acrylate and vinyl acetate which have been buffered to the appropriate pH range, usually present in a weight ratio of about 1:2.5 to about 1:1.2; however, numerous other ethylenically unsaturated monomers can be used, for example, methyl acrylate, ethyl acrylate, methyl methacrylate, styrene, 2-ethylhexylacrylate, vinyl toluene, acrylonitrile, vinylidene chloride, and the like. Minor amounts, i.e., less than about 5 percent by weight, of monomers having a functional group other than an ethylenic group, e.g., acrylic acid, acrylamide, methylol acrylamide, aminoacrylates, or hydroxyethyl acrylates, and the like, can also be present. However, a wide variety of latex paint formulations are suitable vehicles.

Preferably the polymerizable monomers are selected so as to produce a copolymer having a glass transition temperature ($T_g$) below about room temperature so that the individual copolymer particles, when applied on a selected surface as a coating, will coalesce by themselves to provide a substantially continuous polymeric film without the need to apply external heat.

Emulsions of copolymers derived from the aforementioned monomers generally will provide flat-appearing protective and/or decorative coatings. If a degree of surface gloss is desired, polymerizable ethylenically-unsaturated fatty acid esters having an ethylenically-unsaturated aliphatic group of $C_4$ to $C_{20}$ carbon atoms can be copolymerized with the aforementioned monomers as taught in U.S. Pat. No. 3,470,126 to Sekmakas et al.

Illustrative fine particle size latex emulsions suitable for combination with a chromogen to provide a signal coating are disclosed below. Such emulsions can be prepared in a reactor equipped with an agitator, condenser, cooling and heating coils, and addition tubes for the monomers. To form a latex emulsion, the reactor is charged with water containing 70–75% of the total desired amount of a water-soluble polymerization catalyst and a pH regulator or buffer. Thereafter the reactor contents is heated to about 180°–185° F. and a premix of vinyl and/or acrylic monomer is added gradually over a 2–2½ hour period. After the addition of vinyl and/or acrylic monomer is complete, the remainder of the catalyst is added to insure complete reaction, and the mixture is held at 180°–190° F. for ½–1 hour. The pH of the so formed product is adjusted to pH 8.5–9.5 using a 28% aqueous solution of ammonium hydroxide.

The produced latex emulsions may have the following composition:

| | Parts by Weight |
|---|---|
| Water | 40 – 80 |
| Anionic surface active agent | 0.5 – 2 |
| Non-ionic surface active agent | 1 – 4 |
| Vinyl and/or acrylic monomer | 50 – 80 |
| Water soluble catalysts (e.g. potassium persulfate) | 0.05 – 1 |
| Monomer soluble catalysts (e.g. benzoyl peroxide) | 0.05 – 1 |
| Buffer (pH regulator) sodium bicarbonate | 0.05 – 1 |

Suitable anionic surface active agents for the foregoing latex emulsion formulation are sodium octylphenoxy polypropylene oxide sulfonate containing about 20 propylene oxide groups per molecule, sodium dioctyl sulfosuccinate, sodium lauryl sulfate, and the like.

Suitable non-ionic surface active agents for the present purposes are the oxyalkylated alcohols such as octylphenoxy polyoxypropylene ethanol containing about 10 propylene oxide groups per molecule, nonylphenoxy polyoxyethylene ethanol, and the like.

The selection of the particular surface active agents as well as the concentration thereof in a given latex emulsion formulation embodying the present invention depends to some extent also on the type of wall material used for the microcapsules as well as the particle size distribution thereof. However, these parameters for a particular formulation are readily ascertainable by those skilled in the art.

Typical suitable vinyl monomers for the foregoing latex emulsions are vinyl acetate, styrene, vinyl toluene, and the like. Typical suitable acrylic monomers are ethyl acrylate, methyl methacrylate, butyl acrylate, and the like.

The thus produced emulsions are then adjusted for the desired solids content and viscosity, pigmented as desired, and the chromogen combined therewith by admixing immediately or later, e.g., during the addition of pigments or other colorants just prior to use.

The amount of chromogen present in a coating formulation is not overly critical provided a sufficient amount is present to signal ingestion as discussed hereinabove. Of course, the amount of chromogen present should not be so great as to adversely affect the characteristics of the coating formulation itself. Preferably the chromogen is present in an amount of about 0.01 to 3 percent by weight of the formulation and more preferably in an amount of about 0.05 to about 1.5 percent by weight.

For a particular coating formulation the size and amount of chromogen-containing microcapsules are selected so as not to affect substantially the stability, hiding power, tinting strength, burnish resistance, abrasive scrub resistance, stain removal, rheology, adhesion, film coalescence, and color stability of the coating formulation itself. However, the amount and distribution of the chromogen-containing microcapsules should be such as to provide a sufficient number of microcapsules which release the chromogen when a portion of the protective or decorative polymeric film that is formed by the formulation is ruptured.

Other protective and/or decorative coating formulations suitable for use in the preparation of signal coatings in accordance with the present invention are illustrated in U.S. Pat. No. 3,356,654 to Sekmakas, U.S. Pat. No. 3,558,536 to Sekmakas, U.S. Pat. No. 3,817,880 to Kreider, and U.S. Pat. No. 3,819,542 to Kreider.

Suitable chromogens for the purposes of the present invention are those that are physiologically acceptable for ingestion and which produce a color reaction with an activator substance that is present at the time of mastication or ingestion.

Exemplary of such chromogens are amino acid-sensitive, color-producing reagents that are capable of reacting with the amino acids that are normally present in saliva, for example, ninhydrin, isatin, alloxan, and the like.

Another grouping of suitable chromogens comprises the leuco bases and color bases of a dye which, when masticated or ingested, produce a contrasting color. Illustrative of such compounds are the white or colorless moieties of triphenylmethane dyes such as the leuco forms of Crystal Violet, benzaurin, Malachite Green, and the like, of xanthene dyes, e.g., the leuco forms of Rhodamine B, Erythrosine, and the like, of thiazine dyes, e.g., the leuco forms of Methylene Blue, Brilliant Blue, and the like. Also suitable are the white or colorless forms of Fast Green (FD&G Green No. 3).

Metallochromic indicators which give a color reaction in the presence of metal ions normally present in saliva or present in saliva when an undesirable substance such as lead-based paint has been ingested are also suitable chromogens for the present purposes. Metallochromic indicators are materials that, upon forming a complex or chelated with metal ions, develop a color or undergo a color change. These indicators are analogous to the pH indicator dyes and, in fact, are often derivatives of such dyes. The metallochromic indicators, as a class, are quite sensitive to the presence of metal ions; concentrations of about $10^{-6}$ to about $10^{-5}$ moles/liter usually are sufficient to give a detectable color change. A large number of the metallochromic indicators are derivatives of triphenylmethane dyestuffs. Illustrative metallochromic indicators are phthalein violet, xylenol orange, methylthymol blue, metallochrome violet A, and the like. Also suitable are bromopyrogallol read, gallocyanine, dyes derived from fluoroscein, the azo dyes such as Acid chrome blue K, Erio SE, Erio chrome violet, Solochrome fast violet B, Erio chrome black PV, Erio A, Brilliant congo blue, and the like.

In addition, physiologically acceptable color indicators such as phenolphthalein or derivatives thereof, e.g., 3',3'',5',5''-tetrakis-{[bis(carboxymethyl)amino]methyl}phenolphthalein, and the like, can also be utilized as the chromogen.

Suitable acerbic agents that can be incorporated into the signal coating formulations of this invention are sucrose octaacetate, and the like.

The following examples illustrate the compounding of masked chromogen-containing protective coating formulations and the preparation of microencapsulated chromogens.

EXAMPLE I

Signal Coating Containing Crystal Violet Lactone

Pressure-rupturable microcapsules containing Crystal Violet lactone [6-dimethylamino-3,3-bis(p-dimethylaminophenyl)phthalide], i.e., the colorless form of Crystal Violet, are prepared by dissolving the lactone (about 3 wt.-%) in dibutyl phthalate solvent and combining the resulting solution (about 20 parts by weight) with an aqueous 10 wt.-% solution of pigskin gelatin (about 100 parts by weight), and emulsifying the obtained two-phase admixture until the oil-phase droplet size is about 2 to 5 microns. The produced emulsion is maintained at a temperature above about 50° C. to keep the gelatin from gelling.

To induce coacervation, a 20 wt.-% aqueous sodium sulfate solution (about 50 parts by weight) is added slowly to the emulsion while the emulsion is still at above 50° C. so as to deposit the gelatin molecules substantially uniformly about each oil droplet. Thereafter, the heated coacervated mixture is poured into a 7 wt.-% aqueous sodium sulfate solution at about room temperature with agitation. AT this point in time microencapsulation is complete, and the produced microcapsules are filtered, washed with water, and hardened by treatment with a 37 wt.-% aqueous solution of formaldehyde. The hardened microcapsules are filtered, washed, and dried.

The dried microcapsules are incorporated into a pigmented latex interior paint emulsion by stirring the capsules into the otherwise complete emulsion in an amount of about 2 percent by weight thereof to produce a signal coating formulation. Upon mastication by a child of a dried coating produced by applying the formulation on a solid surface, the microcapsules are ruptured, the Crystal Violet lactone is released, and is converted to its colored dye form which stains the child's mouth and tongue.

EXAMPLE II

Signal Coating Containing Brilliant Blue (Leuco Form)

In a manner similar to Example I, the leuco form of Brilliant Blue [10-benzoyl-3,7-bis(dimethylamino)-phenothiazine] (about 4 wt.-%) is dissolved in toluene and microencapsulated using pigskin gelatin. The produced microcapsules are incorporated into a latex-type paint which produces an opaque, coherent film when applied over a surface previously painted with a lead-based paint.

When a fragment of the produced film is masticated by a child, the microcapsules contained therein are ruptured. The microencapsulated, chromogen-containing solution is released in the child's mouth and is converted to its colored form, staining the child's mouth and teeth blue.

EXAMPLE III

Microcapsules of Rhodamine B in Leuco Form Incorporated into a Latex Paint

Ethyl cellulose (about one gram) and the leuco form of Rhodamine B (about 0.05 gram) are dissolved in toluene (about 50 milliliters). The resulting solution is emulsified as fine droplets into ethylene glycol (about 150 milliliters) by rapid stirring for about three hours at room temperature to produce ethyl cellulose microcapsules having an average diameter of about 25 microns and less, and containing the leuco form of Rhodamine B therein.

The produced microcapsules are recovered by centrifugation, rinsed with water, and incorporated into a latex-type paint which produces an opaque coating when applied over a surface previously painted with a lead-based paint. Upon ingestion of the produced opaque coating by a child, the microcapsules are disintegrated, releasing the leuco form of Rhodamine B which, in turn, is converted to its colored dye form upon coming in contact with an aqueous environment.

EXAMPLE IV

Microencapsulation of Erythrosine (Leuco Form) and Formation of a Signal Coating The leuco form of Erythrosine (about 2.5 grams) is dissolved in cottonseed oil (about 50 milliliters) and is admixed with toluene (about 200 milliliters) containing dissolved therein about two grams of polycarbonate. The resulting admixture is then added to glycerine (about 400 milliliters) and emulsified by rapid agitation in a laboratory blender for about four hours at ambient temperature to form microcapsules having an average diameter of about 10 microns and containing the leuco form of Erythrosine. The produced microcapsules are recovered by filtration, washed with water, and thereafter incorporated into a latex-type paint.

Upon ingestion of a fragment of a paint coating formed by the foregoing paint the microcapsules contained therein disintegrate releasing the leuco form of Erythrosine which in turn is converted to the colored dye form upon coming in contact with body fluids.

EXAMPLE V

Microencapsulated Crystal Violet Lactone

A partially condensed urea-formaldehyde thermosetting resin (about 20 grams) is added to a 10-weight percent aqueous solution of polyvinyl alcohol to produce a solution of a cross-linkable reaction product. In addition, a chromogen solution is prepared by dissolving Crystal Violet lactone (about 3 grams) into dibutyl phthalate (about 100 grams).

The produced chromogen solution is then emulsified in the cross-linkable reaction product solution by vigorous agitation for a time period sufficient to produce an emulsion having the chromogen solution as the discontinuous phase and having an average emulsion droplet size of about 3 microns.

Thereafter the agitation rate is reduced to an extent sufficient to maintain a mixing action and glutaraldehyde (about 10 grams) is added to effect cross-linking. After the glutaraldehyde addition the produced admixture is mixed for an additional time period of about 10 minutes and thereafter the produced admixture is heated to an elevated temperature of about 50° C. and maintained at the elevated temperature for about five hours in order to complete the cross-linking.

Thereafter chromogen-bearing microcapsules are recovered from the produced admixture, washed, and incorporated into a latex-type paint formulation. When the paint formulation produced in the foregoing manner is applied to a surface previously painted with a lead-based paint and permitted to dry, an opaque coating containing microencapsulated Crystal Violet lactone obtains.

Upon mastication of the opaque coating by a child, the microcapsules are ruptured and the Crystal Violet lactone chromogen contained therein is released. The chromogen is converted to its colored form when contacted by the child's saliva and stains the child's mouth.

EXAMPLE VI

Microencapsulated Ninhydrin in Latex Paint

Microcapsules containing ninhydrin enclosed in a rupturable polyamide shell are prepared by preparing a first solution comprising terephthaloyl chloride (about 2 grams) in mineral spirits (about 100 grams) and a second solution comprising diethylene triamine (about 5 grams) and ninhydrin in water (about 200 grams). The concentration of ninhydrin in the aqueous solution is about 100 parts per million.

Small droplets of the aforesaid aqueous solution are then extruded into the first solution through a fine orifice (about 0.1 millimeter in diameter) and at a rate greater than the critical fluid velocity for continuous flow through the orifice. As the formed droplets enter the first solution, the droplets become encased in a polyamide shell which is formed at the interface of the droplets and the first solution substantially instantaneously. Thereafter the produced microcapsules are recovered, washed, and are incorporated into a latex-type paint formulation to provide a masked chromogen in a manner similar to Example V.

EXAMPLE VII

Microencapsulated Isatin in Latex Paint

Microcapsules containing isatin encased in a rupturable polyamide shell are prepared by dissolving terephthaloyl chloride (about 2 grams) in mineral spirits (about 100 grams) to form a first solution and by dissolving diethylene triamine (about 5 grams) and isatin in water (about 200 grams) to form an aqueous second solution. The concentration of isatin in the aqueous solution is about 150 parts per million.

The aqueous second solution is then extruded through a 0.1 mm-diameter orifice into the first solution at a rate sufficiently high to form small discrete droplets. As the droplets enter the first solution a polyamide shell is formed substantially instantaneously around the droplets to provide discrete microcapsules containing an aqueous isatin solution. The produced microcapsules are then recovered, washed, and incorporated into a latex-type paint to provide therein an amino acid-sensitive, masked chromogen which gives a color reaction with saliva when the paint is ingested or chewed.

EXAMPLE VIII

Microencapsulated Alloxan in Paint

Rupturable microcapsules containing alloxan within a polyamide shell are prepared by first dissolving terephthaloyl chloride (about 2 grams) in mineral spirits (about 100 grams) and by dissolving diethylene triamine (about 5 grams) and alloxan in water (about 200 grams). The concentration of alloxan in the produced aqueous solution is about 250 parts per million.

The produced aqueous solution is then sprayed through a nozzle and in the form of fine droplets into the terephthaloyl chloride solution. As the droplets enter the first solution, polymerization takes place substantially instantaneously at the interface of the droplets and the terephthaloyl chloride solution and a polyamide shell envelops each droplet to form discrete microcapsules containing an aqueous solution of alloxan. The microcapsules are subsequently collected, washed, and incorporated into a paint formulation to provide therein a masked, amino acid-sensitive chromogen.

I claim:

1. An aqueous latex coating composition comprising an aqueous continuous phase having stably suspended therein coalescable polymeric particles, a pigment, and signal means including a physiologically acceptable chromogen present in an amount sufficient to signal ingestion and in a form not visually discernible in said composition but capable of producing a contrasting color upon contacting an activator substance upon ingestion.

2. The composition in accordance with claim 1 wherein the signal means is contained within disintegratable microcapsules.

3. The composition in accordance with claim 1 wherein the chromogen is a liquid or water-soluble substance which is generally white or colorless and which converts to a colored form upon contact with body fluids.

4. The composition in accordance with claim 3 wherein said chromogen is in liquid form and is contained within microcapsules.

5. The composition in accordance with claim 2 wherein the microcapsules are pressure-rupturable.

6. The composition in accordance with claim 2 wherein said aqueous continuous phase is alkaline and wherein said microcapsules are soluble in an acidic medium but insoluble in an alkaline medium.

7. The composition in accordance with claim 2 wherein said chromogen is colorless while contained within said microcapsules and converts to a colored form upon contact with a body fluid.

8. The composition in accordance with claim 2 wherein said chromogen is substantially white while contained within said microcapsules and converts to a colored form upon contact with a body fluid.

9. The composition in accordance with claim 2 wherein the microcapsules are soluble in gastro-intestinal juices.

10. The composition in accordance with claim 2 wherein the chromogen produces a contrasting color upon physical rupture of the microcapsules and contact with lead-based paint.

11. The composition in accordance with claim 1 additionally containing an acerbic agent.

12. The composition in accordance with claim 1 wherein the chromogen is a leuco base of a non-toxic dye.

13. The composition in accordance with claim 12 wherein the dye is an xanthene dye.

14. The composition in accordance with claim 12 wherein the dye is a thiazine dye.

15. The composition in accordance with claim 12 wherein the dye is a triphenylmethane dye.

16. The composition in accordance with claim 1 wherein the chromogen is an amino acid-sensitive, color-producing reagent.

17. The composition in accordance with claim 1 wherein the chromogen is a metallochromic indicator.

18. The composition in accordance with claim 1 wherein the chromogen produces a contrasting color upon mastication and contact with saliva.

19. The composition in accordance with claim 1 wherein the chromogen produces a contrasting color upon ingestion and contact with gastric juices.

20. A dry signal coating comprising a substantially continuous polymeric film comprising coalesced latex particles having incorporated therein a masked, physiologically acceptable chromogen which normally is not visually discernible but which, upon release when the polymer film is ruptured, produces a contrasting color upon contacting an activator substance upon ingestion; said chromogen being present in an amount sufficient to signal ingestion.

21. The signal coating in accordance with claim 20 wherein said chromogen is contained within discrete, pressure-rupturable microcapsules.

22. The signal coating in accordance with claim 20 wherein said polymeric film additionally contains a pigment.

23. The composition in accordance with claim 1 wherein the chromogen is present in an amount of about 0.01 to about 3 percent by weight of the composition.

24. The composition in accordance with claim 1 wherein the chromogen is present in an amount of about 0.05 to about 1.5 percent by weight of the composition.

* * * * *